United States Patent [19]

Thiem et al.

[11] Patent Number: 4,751,291

[45] Date of Patent: Jun. 14, 1988

[54] PROCESS FOR THE PREPARATION OF GLYCOSYL FLUORIDES PROTECTED ON THE OXYGEN

[75] Inventors: Joachim Thiem, Münster; Hans-Matthias Deger, Hofheim am Taunus; Wolfram Fritsche-Lang, Bensheim; Matthias Kreuzer, Münster, all of Fed. Rep. of Germany

[73] Assignee: Hoechst Aktiengesellschaft, Fed. Rep. of Germany

[21] Appl. No.: 906,547

[22] Filed: Sep. 12, 1986

[30] Foreign Application Priority Data

Sep. 14, 1985 [DE] Fed. Rep. of Germany ....... 3532883
Aug. 1, 1986 [DE] Fed. Rep. of Germany ....... 3626028

[51] Int. Cl.$^4$ ...................... C07H 5/02; C07H 13/00; C07H 15/00
[52] U.S. Cl. .................................... 536/18.6; 536/18.4
[58] Field of Search .............................. 536/18.4, 18.6

[56] References Cited

U.S. PATENT DOCUMENTS 4,659,810  4/1987  Thiem et al. ......................... 536/22

OTHER PUBLICATIONS

A. A. E. Penglis (Adv. Carbohydr. Chem. Biochem., 38, 195–285 (1981).
A. B. Foster and J. H. Westwood (Pure Appl. Chem., 35, 147–168 (1973).
A. Bertho (Ber. Dtsch. Chem. Ges., 63, 836 (1930)).
Chemical Abstracts, 73, (1970), 35645y.
Carbohydrate Research, 132, (1984), pp. 339–341.
Chemical Abstracts, 80, (1974), 96243q.
Chemical Abstracts, 95, (1981), 43491q.

*Primary Examiner*—Ronald W. Griffin
*Attorney, Agent, or Firm*—Finnegan, Henderson, Farabow, Garrett and Dunner

[57] ABSTRACT

Glycosyl halides which are O-acylated or O-alkylated at least in the 2-position are transhalogenated with alkali metal hydrogen difluorides in a polar-aprotic solvent and, if appropriate, the product is anomerized with the addition of less than the stoichiometric amounts of an inorganic fluoride with a Lewis acid character. Depending on the substrate, the glycosyl fluorides with the 1,2-trans or 1,2-cis configuration are obtained.

17 Claims, No Drawings

PROCESS FOR THE PREPARATION OF GLYCOSYL FLUORIDES PROTECTED ON THE OXYGEN

Glycosyl fluorides which are protected on the oxygen, that is to say acylated or alkylated, are exceptionally useful glycosylating reagents in carbohydrate chemistry. It is known that these compounds can be prepared by reacting, for example, O-peracylated monosaccharides with hydrogen fluoride or reacting protected saccharides with a free anomeric hydroxyl group with fluorinating agents, such as pyridine polyhydrofluoride or diethylaminosulfur trifluoride (DAST). According to the prior art, which is reviewed in, for example, articles by A. A. E. Penglis (Adv. Carbohydr. Chem. Biochem. 38, 195-285 (1981)) or A. B. Foster and J. H. Westwood (Pure Appl. Chem. 35, 147-168 (1973)), however, the α-anomers are almost always formed here. The β-anomers, which are at least as interesting from the preparative point of view, cannot be prepared in this manner, but must in general be obtained by transhalogenation from the corresponding chlorine or bromine compounds. The only known reagent for this is silver fluoride, which is expensive and, in addition, sensitive to hydrolysis. Thus, for example, 2,3,4,6-tetra-O-acetyl-β-D-glucopyranosyl fluoride is prepared by reacting acetobromoglucose with AgF in accordance with the method of A. Bertho (Ber. Dtsch. Chem. Ges. 63, 836 (1930)).

It is thus found that the prior art for the preparation of glycosyl fluorides protected on the oxygen is characterized either by the use of hydrogen fluoride, a reagent which is difficult to handle, or by the preparative effort which must be expended on the preparation of suitable starting substances, in particular saccharides selectively unprotected in the 1-position, so that they can then be reacted with fluorinating agents such as pyridine polyhydrofluoride or DAST, which likewise are not without problems, or by the high costs associated with the use of silver fluoride.

It has now been found, surprisingly, that transhalogenation of a glycosyl halide which is protected on the oxygen in at least the 2-position, that is to say acylated or alkylated, is also possible with the aid of alkali metal hydrogen difluorides if the reaction is carried out in the presence of a polar-aprotic solvent. As is already known of transhalogenation reactions by means of silver fluoride (cf A. A. E. Penglis, loc. cit.), the 1,2-transfluoride is formed here too from a substrate which is O-acylated at least in the 2-position. On the other hand, in the case of O-alkylated substrates, an anomerization into the cis form as a rule already takes place in situ. However, the cis form can also frequently be produced in the transhalogenation of O-acylated substrates if less than stoichiometric amounts of an inorganic fluoride with a Lewis acid character are used in addition to the alkali metal hydrogen difluoride.

The invention consequently relates to a process for the preparation of glycosyl fluorides which have the 1,2-trans or 1,2-cis configuration and are O-acylated or O-alkylated at least in the 2-position, by transhalogenation, which comprises reacting the corresponding O-acylated or O-alkylated glycosyl halides with alkali metal hydrogen difluorides in a polar-aprotic solvent and, if appropriate, anomerizing the product with the addition of less than the stoichiometric amounts of an inorganic fluoride with a Lewis acid character. The halogen atom in the glycosyl halides which are to be employed in the process according to the invention and are protected on the oxygen has an atomic weight of at least 35, and is preferably chlorine or bromine.

The glycosyl halides to be employed in the process according to the invention are O-acylated or O-alkylated at least in the 2-position. However, it is preferable to use those glycosyl halides in which all the hydroxyl groups are protected, that is to say which are peracylated or peralkylated. Examples of acyl radicals which may be mentioned are acetyl, chloroacetyl, bromoacetyl, propionyl, butyryl, pivaloyl and benzoyl, p-methoxybenzoyl and o- and p-nitrobenzoyl. Possible alkyl radicals are groups of the general formula —$CR^1R^2R^3$, in which the substituents $R^1$, $R^2$ and $R^3$ are identical or different and can denote hydrogen, alkyl or alkenyl with in each case up to 20 carbon atoms, and aryl or a polynuclear aromatic system with up to 25 carbon atoms, which can in each case also contain, in the nucleus, radicals with one or more electron-withdrawing or electron-repelling substituents, such as methoxy, methyl, halogen, nitro or nitrile groups.

The glycosyl halides mentioned, which are protected on the oxygen and can be used as starting substances, can be derived from monosaccharides, such as glucose, galactose, mannose, gulose, talose, allose, altrose and the like, including the $C_5$-aldoses, such as xylose, ribose and the like, and from oligosaccharides, in particular disaccharides, such as lactose, maltose, cellobiose or gentiobiose, or from higher oligosaccharides, such as maltotriose or maltotetraose.

Of the alkali metal hydrogen difluorides which can be used according to the invention for the purpose of the transhalogenation, potassium hydrogen difluoride is preferred.

Polar-aprotic solvents which may be mentioned for the process according to the invention are, in particular, the nitriles, if these can be used as solvents, such as, for example, aceto-, propio- or benzonitrile, and furthermore nitrohydrocarbons, such as nitromethane, nitrobenzene and nitrotoluene, as well as mixtures thereof with nonpolar aprotic solvents, thus, for example, mixtures of acetonitrile with dichloromethane or chloroform.

Inorganic fluorides with a Lewis acid character which can be added in the process according to the invention are, for example, $BF_3$, $SnF_4$, $ZrF_4$ or, preferably, $TiF_4$, these Lewis acids being used in particular in less than 25% of the stoichiometric amount.

The transhalogenation according to the invention is in general carried out under atmospheric pressure, advantageously between 10° C. and 100° C., preferably between 40° C. and 80° C. It is possible, but not preferred, to use increased or reduced pressure.

The process according to the invention is illustrated, but not limited, by the embodiment examples given below.

EXAMPLES (1) Preparation of 2,3,4,6-tetra-O-acetyl-β-D-glucopyranosyl fluoride 10.0 g (24.8 mmol) of 2,3,4,6-tetra-O-acetyl-α-D-glucopyranosyl bromide were heated under reflux with 10.0 g (128 mmol) of potassium hydrogen difluoride in 50 ml of absolute acetonitrile. After 24 hours, the mixture was filtered, the solvent was stripped off in vacuo and the residue was taken up in chloroform. Washing three times with water and drying over magnesium sulfate gave 7.4 g of crude product, which, according to thin layer chromatography (TLC) (toluene/ethyl acetate, 1:1) contained traces of hydrolysis products in addition to 2,3,4,6-tetra-O-acetyl-β-D-glucopyranosyl fluoride. Purification was by recrystallization from diethyl ether. Yield 5.9 g (70%), melting point 88°–89° C., $[\alpha]_D = +20$ (c=1.0 in chloroform) [A. Bertho, loc. cit.; melting point 89° C., $[\alpha]_D = +21.9$ (chloroform)].

(2) Preparation of 2,3,4,6-tetra-O-acetyl-β-D-galactopyranosyl fluoride 10.0 g (24.3 mmol) of 2,3,4,6-tetra-O-acetyl-α-D-galactopyranosyl bromide were heated under reflux in 100 ml of anhydrous acetonitrile with 10.0 g (128 mmol) of potassium hydrogen difluoride for 6 hours. The mixture was then filtered, the solvent was stripped off in vacuo and the residue was taken up in methylene chloride. After filtration over a short silica gel column and concentration of the solution, it was possible to crystallize the product from ether. Yield 6.1 g (72%), melting point 100° C., $[\alpha \cdot_D{}^{20}] = +17.5$ (c=1.03 in CHCl$_3$) [F. Micheel et al., Chem. Ber. 88, 475 (1955), melting point 98°–99° C., $[\alpha]_D{}^{18} = +22$ (CH$_3$OH)]. $^1$H NMR (CDCl$_3$): $\delta = 5.26$ (dd, 1-H), $J_{1,2} = 7.0$, $J_{1,F} = 50.0$ Hz.

(3) Preparation of 2,3,4,6-tetra-O-acetyl-α-D-mannopyranosyl fluoride 8.7 g (21.2 mmol) of 2,3,4,6-tetra-O-acetyl-α-D-mannopyranosyl bromide were dissolved in 30 ml of anhydrous acetonitrile and the solution was heated under reflux with 5.0 g (64 mmol) of potassium hydrogen difluoride. After 3 hours, the starting material was no longer detectable (TLC: methylene chloride/ether, 9:1). The solution was filtered and concentrated and the crude product was recrystallized from ether. Yield 5.74 g (77%), melting point 65°–67° C., $[\alpha]_D{}^{20} = +21.2$ (c=1.07 in chloroform) [A. Bertho, loc. cit.: melting point 68°–69° C., $[\alpha]_{DS}{}^{20} = +21.5$ (chloroform)]. $^1$H NMR (CDCl$_3$): $\delta = 5.58$ (dd, 1-H), $J_{1,2} = 1.9$, $J_{1,F} = 48.4$ Hz; [L. D. Hall et al., Can. J. Chem. 47, 1 (1969): $\delta = 5.57$ (dd, 1-H), $J_{1,2} = 1.7$, $J_{1,F} = 48.6$ Hz].

(4) In situ anomerization of 2,3,4,6-tetra-O-acetyl-β-D-galactopyranosyl fluoride 10.0 g (24.3 mmol) of 2,3,4,6-tetra-O-acetyl-α-D-galactopyranosyl bromide were heated under reflux with 10.0 g (128 mmol) of potassium hydrogen difluoride and 0.5 g (4 mmol) of titanium tetrafluoride in 50 ml of thoroughly dried acetonitrile for 10 hours. The solution, which became dark-colored in the course of the reaction, was filtered and concentrated, the residue was taken up in methylene chloride and the mixture was filtered again over 20 g of silica gel. The crude product was purified by chromatography (silica gel, n-hexane/ethyl acetate, 2:1). Yield 2.7 g (32%) of 2,3,4,6-tetra-O-acetyl-α-D-galactopyranosyl fluoride. $^1$H NMR (CDCl$_3$): $\delta = 5.81$ (dd, 1-H), $J_{1,2} = 2.7$, $J_{1,F} = 52.8$ Hz.

(5) Preparation of 2,3,4,6-tetra-O-benzyl-α-D-glucopyranosyl fluoride (a) 3.0 g (5.5 mmol) of 2,3,4,6-tetra-O-benzyl-D-glucopyranose were dissolved in 30 ml of anhydrous methylene chloride and the solution was stirred with 1.45 ml (2.11 g; 16.5 mmol) of oxalyl dichloride and 0.3 ml of dimethylformamide at room temperature. After one hour, the solution was concentrated under a high vacuum, the residue was taken up in 10 ml of methylene chloride and the mixture was filtered over about 10 g of silica gel. Renewed concentration gave 2.48 g (80%) of 2,3,4,6-tetra-O-benzyl-α-D-glucopyranosyl chloride as a colorless syrup. The crude product was taken up in 20 ml of anhydrous acetonitrile and the mixture was heated under reflux with 3.0 g (38 mmol) of potassium hydrogen fluoride (24 hours at 100° C., dried over P$_2$O$_5$) for 8 hours. It was possible to purify the crude product by column chromatography on silica gel (methylene chloride/ether, 20:1). Yield: 1.1 g (47%) of 2,3,4,6-tetra-O-benzyl-α-D-glucopyranosyl fluoride.

We claim:

1. A process for the preparation of a 1,2-trans- or -cis-glycosyl fluoride which is O-acylated or O-alkylated at least in the 2-position, by transhalogenation, which comprises reacting the corresponding O-acylated or O-alkylated glycosyl halide with an alkali metal hydrogen difluoride in a polar-aprotic solvent and anomerizing the product by addition of less than the stoichiometric amount of an inorganic fluoride with a Lewis acid character.

2. The process as claimed in claim 1, wherein a chloride or bromide is employed as the glycosyl halide.

3. The process as claimed in claim 1, wherein a glycosyl halide in which all the hydroxyl groups are protected is employed.

4. The process as claimed in claim 1, wherein potassium hydrogen difluoride is employed as the alkali metal hydrogen difluoride.

5. The process as claimed in claim 1, wherein the inorganic fluoride with a Lewis acid character is used in less than 25% of the stoichiometric amount.

6. The process as claimed in claim 1, which is carried out at a temperature in the range of from 10° C. to 100° C.

7. The process as claimed in claim 1, which is carried out at a temperature in the range of from 40° C. to 80° C.

8. A process for the preparation of a 1,2-trans- or -cis-glycosyl fluoride which is O-acylated dor O-alkylated at least in the 2-position, by transhalogenation, which comprises reacting the corresponding O-acylated or O-alkylated glycosyl halide with an alkali metal hydrogen difluoride in a polar-aprotic solvent and anomerizing the product by addition of less than the stoichiometric amount of BF$_3$, SnF$_4$, ZrF$_4$ or TiF$_4$.

9. The process as claimed in claim 8, wherein TiF$_4$ is employed as an inorganic fluoride with a Lewis acid character.

10. The process as claimed in claim 8, which is carried out at a temperature in the range of from 10° C. to 100° C.

11. The process as claimed in claim 8, which is carried out at a temperature in the range of from 40° C. to 80° C.

12. A process for the preparation of a 1,2-trans- or -cis-glycosyl fluoride which is O-acylated or O-alkylated at least in the 2-position, by transhalogenation, which comprises reacting the corresponding O-acylated or O-alkylated glycosyl halide with an alkali metal hydrogen difluoride in a polaraprotic solvent.

13. The process as claimed in claim 12, wherein a chloride or bromide is employed as the glycosyl halide.

14. The process as claimed in claim 12, wherein a glycosyl halide in which all the hydroxyl groups are protected is employed.

15. The process as claimed in claim 12, wherein potassium hydrogen difluoride is employed as the alkali metal hydrogen difluoride.

16. The process as claimed in claim 12, which is carried out at a temperature in the range of from 10° C. to 100° C.

17. The process as claimed in claim 12, which is carried out at a temperature in the range of from 40° C. to 80° C.

* * * * *